US012778861B2

(12) United States Patent
Yamaguchi

(10) Patent No.: US 12,778,861 B2
(45) Date of Patent: Nov. 3, 2026

(54) WATER-IN-OIL TYPE EMULSION COSMETICS

(71) Applicant: AJINOMOTO CO., INC., Tokyo (JP)

(72) Inventor: Eriko Yamaguchi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 639 days.

(21) Appl. No.: 18/159,862

(22) Filed: Jan. 26, 2023

(65) Prior Publication Data

US 2023/0233423 A1 Jul. 27, 2023

(30) Foreign Application Priority Data

Jan. 26, 2022 (JP) ................................ 2022-010466

(51) Int. Cl.

| | |
|---|---|
| ***A61K 8/06*** | (2006.01) |
| ***A61K 8/02*** | (2006.01) |
| ***A61K 8/25*** | (2006.01) |
| ***A61K 8/26*** | (2006.01) |
| ***A61K 8/29*** | (2006.01) |
| ***A61K 8/31*** | (2006.01) |
| ***A61K 8/37*** | (2006.01) |
| ***A61K 8/44*** | (2006.01) |
| ***A61K 8/49*** | (2006.01) |
| ***A61K 8/88*** | (2006.01) |
| ***A61Q 1/02*** | (2006.01) |

(52) U.S. Cl.

CPC .............. *A61K 8/064* (2013.01); *A61K 8/022* (2013.01); *A61K 8/25* (2013.01); *A61K 8/26* (2013.01); *A61K 8/29* (2013.01); *A61K 8/31* (2013.01); *A61K 8/37* (2013.01); *A61K 8/44* (2013.01); *A61K 8/4973* (2013.01); *A61K 8/88* (2013.01); *A61Q 1/02* (2013.01); *A61K 2800/412* (2013.01); *A61K 2800/43* (2013.01); *A61K 2800/614* (2013.01)

(58) Field of Classification Search

CPC .......... A61K 8/064; A61K 8/022; A61K 8/25; A61K 8/26; A61K 8/29; A61K 8/31; A61K 8/37; A61K 8/44; A61K 8/4973; A61K 8/88; A61K 2800/412; A61K 2800/43; A61K 2800/614; A61K 8/025; A61K 8/585; A61K 8/731; A61K 8/87; A61Q 1/02

See application file for complete search history.

(56) References Cited

FOREIGN PATENT DOCUMENTS

| | | | | |
|---|---|---|---|---|
| JP | 11-139954 | A | | 5/1999 |
| JP | 2001-97888 | A | | 4/2001 |
| JP | 2004-51629 | A | | 2/2004 |
| JP | 2004-175709 | A | | 6/2004 |
| JP | 2004175709 | | * | 6/2004 |
| JP | 2004-210765 | A | | 7/2004 |
| JP | 2004210765 | | * | 7/2004 |
| JP | 2012-46434 | A | | 3/2012 |
| JP | 2018-70556 | A | | 5/2018 |
| JP | 2019-19077 | A | | 2/2019 |
| JP | 2020-94012 | A | | 6/2020 |
| WO | WO2003078507 | | * | 9/2003 |
| WO | WO 2018/062315 | A1 | | 4/2018 |

OTHER PUBLICATIONS

Japanese Notice of Reasons for Refusal issued Nov. 11, 2025 in Japanese Patent Application No. 2022-010466 (with computer-generated English Translation), 8 pages.

"Albion Skin Glazing Foundation (010)", Cosmetic-Info, Retrieved from the Internet: https://www.cosmetic-info.jp/prod/detail.php?id=62140, Aug. 18, 2018, 6 pages (with concise explanation).

"Excia AL superior Cream Foundation EX (NA200)", Cosmetic—Info, Retrieved from the Internet: https://www.cosmetic-info.jp/prod/detail.php?id=54663, Sep. 18, 2017, 7 pages (with concise explanation).

Basic information, purpose of blending and safety of polymethylsilsesquioxan, Cosmetic Ingredient Information Online, Retrieved from the Internet; https://cosmetic-ingredients.org/texture-enhancer/7410/, Feb. 21, 2023, 9 pages (with concise explanation).

* cited by examiner

*Primary Examiner* — Robert A Wax
*Assistant Examiner* — Kimberly Barber
(74) *Attorney, Agent, or Firm* — Oblon, McClelland, Maier & Neustadt, L.L.P.

(57) ABSTRACT

Water-in-oil type emulsion cosmetics containing (a) polyaspartic acid or a salt thereof, (b) a spherical powder, (c) an oily component, (d) a lipophilic surfactant, (e) a pigment, and (f) water can achieve superior makeup effects, good moist feeling, superior emulsion stability and pigment dispersibility.

11 Claims, No Drawings

WATER-IN-OIL TYPE EMULSION COSMETICS

CROSS REFERENCES TO RELATED APPLICATIONS

This application claims priority to Japanese Patent Application No. 2022-010466, filed on Jan. 26, 2022, which is incorporated herein by reference in its entirety.

BACKGROUND OF THE INVENTION

Field of the Invention

The present invention relates to water-in-oil type emulsion cosmetics containing pigments.

Discussion of the Background

Emulsion cosmetics containing pigments, such as liquid foundations, are easy to spread evenly on the skin and easily achieve good makeup effects. In addition, treatment effects can be easily imparted to cosmetic formulations since active ingredients can be blended relatively freely in the aqueous phase and oil phase. For these reasons, emulsion cosmetics containing pigments are highly popular formulations in the makeup cosmetics market.

Emulsion cosmetics are roughly classified into water-in-oil type (W/O type) emulsion cosmetics and oil-in-water type (O/W type) emulsion cosmetics. Emulsion cosmetics containing pigments are required to have resistance to sweat and moisture in order to keep the cosmetic film beautiful for a longer period of time. From the aspect of water resistance, it is preferable to use an inorganic pigment subjected to a hydrophobic treatment of the surface or an emulsifier with a low HLB value as a component of the emulsion cosmetic. Thus, a water-in-oil type emulsion that can easily contain such components is often selected.

However, the water-in-oil type emulsion cosmetics contain a larger amount of oily components than the oil-in-water type emulsion cosmetics. Therefore, they tend to cause a sticky feeling and a glossy finish.

Given the above, attempts have been made to blend a spherical powder that can confer a soft focus effect and a foggy texture to cosmetics by diffuse reflection, and can achieve improvement effects on sensory aspects such as elongation at the time of application and a dry touch after application.

In water-in-oil type emulsion cosmetics containing pigments, when a large amount of inorganic pigments are blended for the purpose of obtaining high covering power and UV scattering effect, dispersibility of such pigments deteriorates, and problems occur such as decreased color developing property of the cosmetics, decreased stability over time, and a dry feeling due to a powdery finish.

Therefore, taking note of polyaspartate, which is a highly safe moisturizing agent with high biocompatibility, superior skin compatibility, and moisturizing performance, a water-in-oil type emulsion composition containing a specific silicone-based surfactant, silicone oil, and polyaspartate (see JP-A-2004-051629, which is incorporated herein by reference in its entirety) and a water-in-oil type emulsion cosmetic containing polyoxyethylene dipolyhydroxystearate and polyaspartate (see JP-A-2004-210765, which is incorporated herein by reference in its entirety) have been proposed in order to improve the feel and moist feeling during use and stability over time.

However, since polyaspartate is an electrolyte polymer with strong cohesive property, it is difficult to stably blend polyaspartate in an emulsion composition, and peptide bonds are cleaved under acidic conditions to cause a decrease in the molecular weight. Such problems limit the use and the amount of polyaspartate to be blended.

Furthermore, since polyaspartate is superior in pigment dispersibility and dispersion stability in an aqueous system, it is effective in improving, in cosmetics containing pigments, color developing property of the pigments and stability over time by suppressing aggregation of the pigments. Utilizing such features, addition of polyaspartate to a cosmetic pigment dispersion has also been proposed (see JP-A-2004-175709, which is incorporated herein by reference in it is entirety).

However, the pigment dispersing effect of polyaspartate also increases the glossiness of the cosmetic coating film. In cosmetics required to achieve a soft focus effect or a matte finish, therefore, polyaspartate problematically impairs the desired finish.

In view of the above, there is a demand for a water-in-oil type emulsion cosmetic that has good makeup effects such as covering power and soft focus effect, good moisture feeling, superior emulsion stability, and pigment dispersibility.

SUMMARY OF THE INVENTION

Accordingly, it is one object of the present invention to provide a water-in-oil type emulsion cosmetic containing pigments, which has good makeup effects such as covering power and soft focus effect, good moist feeling, and good emulsion stability.

It is another object of the present invention to provide a water-in-oil type emulsion cosmetic which is superior in pigment dispersibility.

These and other objects, which will become apparent during the following detailed description, have been achieved by the present inventor's discovery that a water-in-oil type emulsion cosmetic containing (a) polyaspartic acid or a salt thereof, (b) a spherical powder, (c) an oily component, (d) a lipophilic surfactant, (e) a pigment, and (f) water provides good makeup effects such as covering power and soft focus effect, as well as a good moist feeling, and improves emulsion stability, and further improves pigment dispersibility, which resulted in the completion of the present invention.

That is, the present invention provides the following.

(1) A water-in-oil type emulsion cosmetic comprising (a) polyaspartic acid or a salt thereof, (b) a spherical powder, (c) an oily component, (d) a lipophilic surfactant, (e) a pigment, and (f) water.

(2) The emulsion cosmetic of (1), wherein a content ($W_a$) of the (a) polyaspartic acid or a salt thereof is 0.01 mass % to 1 mass % as a content of a free form thereof.

(3) The emulsion cosmetic of (1) or (2), wherein the (b) spherical powder is one or more members selected from the group consisting of spherical silicic anhydride, spherical silicone powder, spherical nylon powder, spherical cellulose powder, and spherical polyurethane powder.

(4) The emulsion cosmetic of any of (1) to (3), wherein the (b) spherical powder has a volume-based average particle size of 0.1 μm to 30 μm.

(5) The emulsion cosmetic of any of (1) to (4), wherein a content ($W_b$) of the (b) spherical powder is 0.1 mass % to 5 mass %.

(6) The emulsion cosmetic of any of (1) to (5), wherein the (c) oily component is one or more members selected from the group consisting of hydrocarbon, ester, and silicone oil.

(7) The emulsion cosmetic of any of (1) to (6), wherein a content ($W_c$) of the (c) oily component is 5 mass % to 60 mass %.

(8) The emulsion cosmetic of any of (1) to (7), wherein the (d) lipophilic surfactant is one or more members selected from the group consisting of glycerol fatty acid ester, sorbitan fatty acid ester, and polyoxyethylene·polyoxypropylene modified alkylmethylpolysiloxane·dimethylpolysiloxane copolymer, each of which has a Hydrophilic-Lipophilic Balance (HLB) value of 3 to 6.

(9) The emulsion cosmetic of any of (1) to (8), wherein a content ($W_d$) of the (d) lipophilic surfactant is 0.1 mass % to 10 mass %.

(10) The emulsion cosmetic of any of (1) to (9), wherein the (e) pigment is an inorganic pigment.

(11) The emulsion cosmetic of any of (1) to (10), further comprising (g) a hydrophilic or water-soluble additive for cosmetics.

(12) The emulsion cosmetic of (11), wherein the (g) hydrophilic or water-soluble additive for cosmetics is one or more members selected from the group consisting of (g-1) amino acid and a salt thereof, (g-2) aliphatic hydroxycarboxylic acid having 1 to 10 carbon atoms and a salt thereof, (g-3) polyhydric alcohol, and (g-4) betaine.

(13) The emulsion cosmetic of any of (1) to (12), having a viscosity of not less than 10 Pas at 25° C.

Effect of the Invention

The present invention can provide water-in-oil type emulsion cosmetics containing pigments. Such cosmetics are superior in makeup effects such as color development, covering power, and soft focus effect of cosmetics, have good moist feeling, and are superior in emulsion stability and pigment dispersibility.

DETAILED DESCRIPTION OF THE PREFERRED EMBODIMENTS

The water-in-oil type emulsion cosmetics of the present invention contain (a) polyaspartic acid or a salt thereof, (b) a spherical powder, (c) an oily component, (d) a lipophilic surfactant, (e) a pigment, and (f) water.

The polyaspartic acid contained as component (a) in the water-in-oil type emulsion cosmetics of the present invention is L-aspartic acid, D-aspartic acid or DL-aspartic acid polymerized by an α-amide bond or a β-amide bond.

For the purpose of the present invention, poly L-aspartic acid and poly DL-aspartic acid are preferably used, and poly L-aspartic acid is more preferably used. In addition, any of an α-amide conjugate, a β-amide conjugate, and a mixture of an α-amide conjugate and a β-amide conjugate can be used, and an α-amide conjugate and a mixture of an α-amide conjugate and a β-amide conjugate are preferably used.

In the present invention, polyaspartic acid with a weight average molecular weight of 1,000 to 100,000 as measured by gel filtration chromatography is used. polyaspartic acid with the aforementioned weight average molecular weight of 2,000 to 50,000 is preferred, 2,000 to 10,000 is more preferred, and 3,000 to 5,000 is further preferred.

In the present invention, a salt of the above-mentioned polyaspartic acid can also be used as component (a).

The salt of polyaspartic acid is not particularly limited as long as it is a pharmaceutically acceptable salt and used for skin compositions. Examples thereof include salts with inorganic bases such as alkali metal salts (e.g., lithium salt, sodium salt, potassium salt, and the like); alkaline earth metal salts (e.g., magnesium salt, calcium salt, and the like); ammonium salt; and the like, and salts with organic bases such as alkanol amine salts (e.g., mono ethanolamine salt, diethanolamine salt, triethanolamine salt, and the like); salts with basic amino acids (e.g., arginine salt, lysine salt, histidine salt, and the like); and the like, and alkali metal salts such as sodium salt and the like are preferably used.

Polyaspartic acid or a salt thereof can be produced by a known method.

For example, a mixture of an α-amide conjugate and a β-amide conjugate can be obtained by a solid state polymerization method including directly heating and condensing amino acid (see The Journal of the American Chemical Society 82 3745 (1960), which is incorporated herein by reference in its entirety, etc.).

A polyamide containing α-amide can be obtained by a method of ring opening the N-carboxy acid anhydride of an amino acid and subjecting same to decarboxylation polymerization (see Journal of Polymer Science A14 2065 (1976) and JP-A-s46-27828, which are incorporated herein by reference in their entireties, etc.), a method of polymerizing an active amino acid ester (see JP-A-s54-47799, which is incorporated herein by reference in its entirety), a method of thermally polymerizing an N-dithiocarbonylalkoxycarbonylamino acid (see JP-B-45-9391, which is incorporated herein by reference in its entirety), and the like.

In addition, a polymer that retains the optical activity of aspartic acid used as a starting material can be obtained by ring-opening polymerization of N-carboxylic anhydride of amino acid.

In the present invention, polyaspartic acid or a salt thereof may be produced and used by the above-mentioned known methods. Alternatively, commercially available products provided by Ajinomoto Co., Inc., etc. can also be used.

In the water-in-oil type emulsion cosmetics of the present invention, one kind of the above-mentioned polyaspartic acid or a salt thereof may be used alone, or two or more kinds thereof may be selected and used in combination.

The content ($W_a$) of component (a) in the water-in-oil type emulsion cosmetics of the present invention is preferably 0.01 mass % to 1 mass %, more preferably 0.03 mass % to 0.9 mass %.

When a polyaspartic acid salt is contained as component (a), the above-mentioned content is shown as a content converted to that of a free form.

A spherical powder contained as component (b) in the water-in-oil type emulsion cosmetics of the present invention can be used without particular limitation as long as it has a spherical shape and can be used for skin compositions.

Examples of such spherical powder include spherical silicic anhydride; spherical silicone powders such as polymethylsilsesquioxane (three-dimensional network crosslinked polymer of methyltrimethoxysilane), (diphenyldimethylpolysiloxane/vinyldiphenyldimethylpolysiloxane/silsesquioxane) crosslinked polymer (crosslinked copolymer consisting of diphenyldimethylpolysiloxane, vinyldiphenyldimethylpolysiloxane, and silsesquioxane), (dimethylpolysiloxane/vinyldimethylpolysiloxane) crosslinked polymer (crosslinked polymer obtained by crosslinking dimethylpolysiloxane with vinyldimethylpolysiloxane), and the like; spherical polymethyl methacrylate powders such as polymethyl methacrylate, crosslinked copolymer of methyl methacrylate and ethylene glycol dimethacrylate, and the like; spherical nylon powders such as spherical nylon-6, spherical nylon-12, and the like; spherical cellulose powder; spherical polyurethane powder; and composite powder obtained by coating the surface of the aforementioned spherical powder with a plate powder, for example, spherical silicone powder coated with plate alumina powder and the like.

From the aspect of improving makeup effects such as soft focus effects, spherical silicic anhydride, spherical silicone powder, spherical nylon powder, spherical cellulose powder, spherical polyurethane powder, and the like are preferably used as the spherical powder.

From the aspect of the soft focus effects and feeling of use when applied to the skin, the spherical powder to be used preferably has a volume-based average particle size of 0.1 μm to 30 μm, more preferably 0.5 μm to 20 μm, further preferably 0.5 μm to 10 μm, as measured by a laser diffraction/scattering method.

Commercially available products provided as cosmetic powders by each company can be used as the above-mentioned spherical powder.

In the present invention, one kind of spherical powder may be selected and used alone, or two or more kinds thereof may be selected and used in combination.

The content ($W_b$) of component (b) in the water-in-oil type emulsion cosmetics of the present invention is preferably 0.1 mass % to 5 mass %, more preferably 0.5 mass % to 3 mass %.

The oily component contained as component (c) in the water-in-oil type emulsion cosmetics of the present invention can be used without particular limitation as long as it is a component generally used as an oily base or an oily emollient component in cosmetics. Examples thereof include animal and plant fats and oils such as olive oil, soybean oil, *camellia* oil, sesame oil, peanuts oil, cacao butter, beef tallow, lard, and the like; waxes such as Carnauba wax, beeswax, jojoba oil, and the like; aliphatic alcohols such as octyldodecanol, cetanol, stearyl alcohol, and the like; fatty acids such as oleic acid, palmitic acid, stearic acid, and the like; hydrocarbons such as squalane, white petrolatum, liquid paraffin, ceresin, microcrystalline wax, and the like; ethers such as glyceryl mono-2-ethylhexyl ether, glyceryl mono-cetyl ether, glyceryl mono-stearyl ether, glyceryl mono-oleyl ether, and the like; esters such as isopropyl myristate, isopropyl palmitate, cetyl 2-ethylhexanoate, (phytosteryl/isostearyl/cetyl/stearyl/behenyl) dimer dilinoleate, isopropyl N-lauroylsarcosinate, di(cholesteryl/2-octyldodecyl) N-lauroyl-L-glutamate, di(cholesteryl/behenyl/2-octyldodecyl) N-lauroyl-L-glutamate, caprylic/capric triglyceride, di(phytosteryl/2-octyldodecyl) N-lauroyl-L-glutamate, di(phytosteryl/2-octyldodecyl/behenyl) N-lauroyl-L-glutamate, glyceryl tristearate, glyceryl tribehenate, and the like; silicone oils such as octamethylcyclotetrasiloxane, decamethylcyclopentasiloxane, dimethylpolysiloxane, methylphenylpolysiloxane, and the like; and the like.

In the present invention, one of the above-mentioned oily components may be selected and used alone, or two or more kinds thereof may be selected and used in combination.

From the aspect of the feeling of use of the water-in-oil type emulsion cosmetic of the present invention, hydrocarbons such as squalane, liquid paraffin, microcrystalline wax, and the like; esters such as di(cholesteryl/2-octyldodecyl) N-lauroyl-L-glutamate, di(cholesteryl/behenyl/2-octyldodecyl) N-lauroyl-L-glutamate, glyceryl tribehenate, and the like; silicone oils such as decamethylcyclopentasiloxane, dimethylpolysiloxane, and the like; and the like are preferably used.

The water-in-oil type emulsion cosmetics of the present invention may contain a lipophilic or oil-soluble additive for cosmetics as the (c) oily component, as necessary.

Examples of such additive for cosmetics include lipophilic or oil-soluble antioxidants such as tocopheryl acetate, dibutyl hydroxytoluene, γ-oryzanol, and the like; lipophilic or oil-soluble antiseptics such as propyl p-hydroxybenzoate, butyl p-hydroxybenzoate, and the like; lipophilic or oil-soluble ultraviolet absorbers such as dihydroxy benzophenone, hexyl diethylaminohydroxybenzoylbenzoate, 2-ethylhexyl paramethoxycinnamate, and the like; lipophilic or oil-soluble flavors such as geraniol, citral, limonene, lavender oil, and the like; lipophilic or oil-soluble dyes such as Red No. 215, Yellow No. 204, β-carotene, chlorophyll, and the like; and the like.

One or more kinds of these can be used according to the purposes.

In the water-in-oil type emulsion cosmetics of the present invention, commercially available products provided as oily raw materials for cosmetics or oil-soluble or lipophilic additives for cosmetics by each company can be used as the above-mentioned oily component.

The content ($W_c$) of the component (c) in the water-in-oil type emulsion cosmetics of the present invention is preferably 5 mass % to 60 mass %, more preferably 10 mass % to 40 mass %.

The lipophilic surfactant contained as component (d) in the water-in-oil type emulsion cosmetics of the present invention can be used without particular limitation as long as it is a surfactant that is well mixed with the above-mentioned (c) oily component and functions as a water-in-oil type emulsifier. For example, lipophilic non-ionic surfactants including glycerol fatty acid esters such as glyceryl monostearate, glyceryl monoisostearate, glyceryl monooleate, and the like; polyglycerol fatty acid esters such as diglyceryl monostearate, diglyceryl monoisostearate, diglyceryl monooleate, decaglyceryl tristearate, decaglyceryl trioleate, decaglyceryl pentastearate, decaglyceryl pentaisostearate, tetraglyceryl monostearate, tetraglyceryl monooleate, decaglyceryl pentaoleate, and the like; propylene glycol ester of fatty acids such as propylene glycol monostearate and the like; sorbitan fatty acid esters such as sorbitan monolaurate, sorbitan monopalmitate, sorbitan monostearate, sorbitan monoisostearate, sorbitan monooleate, sorbitan sesquistearate, sorbitan sesquiisostearate, sorbitan sesquioleate, sorbitan tristearate, sorbitan trioleate, and the like; polyethylene glycol fatty acid esters such as polyethylene glycol monostearate (2E.O.), polyethylene glycol mono stearate (4E.O.), polyethylene glycol monooleatate (6E.O.), and the like; polyoxyethylene hydrogenated castor oils such as polyoxyethylene hydrogenated castor oil (5E.O.), polyoxyethylene hydrogenated castor oil (10E.O.), and the like; polyoxyethylene sorbitol fatty acid esters such as polyoxyethylene sorbitol tetraoleate (6E.O.) and the like; polyoxyethylene alkyl ethers such as polyoxyethylene cetyl ether (2E.O.), polyoxyethylene stearyl ether (2E.O.), polyoxyethylene alkyl (carbon number 12-14) ether (3E.O.), polyoxyethylene behenyl ether (5E.O.), and the like; polyoxyethylene alkenyl ethers such as polyoxyethylene oleyl ether (2E.O.) and the like; polyoxyethylene polyoxypropylene alkyl ethers such as polyoxyethylene (12E.O.) polyoxypropylene (6P.O.) decyltetradecyl ether and the like; and the like, silicone-based surfactants such as polyoxyethylene (10E.O.)·polyoxypropylene (1P.O.) modified cetyl methylpolysiloxane·dimethylpolysiloxane copolymer and the like, and the like are preferred surfactants.

In the present invention, one kind of the above-mentioned lipophilic surfactant may be selected and used alone, or two or more kinds thereof may be selected and used in combination.

From the aspect of the emulsion stability of the water-in-oil type emulsion cosmetics, glycerol fatty acid ester, sorbitan fatty acid ester, polyoxyethylene·polyoxypropylene modified alkylmethylpolysiloxane·dimethylpolysiloxane copolymer, and the like, each having a Hydrophilic-Lipophilic Balance (HLB) value of about 3 to 6, are more preferably used as the lipophilic surfactants.

In the water-in-oil type emulsion cosmetics of the present invention, commercially available products provided as surfactants for cosmetics by each company can be used as the lipophilic surfactant.

The content ($W_a$) of component (d) in the water-in-oil type emulsion cosmetics of the present invention is preferably 0.1 mass % to 10 mass %, more preferably 1 mass % to 7 mass %.

A pigment contained in the water-in-oil type emulsion cosmetics of the present invention as component (e) is a powder used for coloration, retention of the shape of the cosmetics, imparting and adjusting color tone, glossiness, feeling of use (spreadability, adhesiveness, slipperiness, etc.), and insoluble in water and oil, and is a powder other than the above-mentioned (b) spherical powder.

As such pigment, any powder can be used without particular limitation as long as it is generally used as an extender pigment, a white pigment, a coloring pigment, a pearlescent pigment, or the like in cosmetics and does not fall under the above-mentioned (b) spherical powder. Inorganic pigments are preferably used.

Examples of the inorganic pigment preferably contained as component (e) in the water-in-oil type emulsion cosmetics of the present invention include silicic anhydride, silicate (talc, kaolin, mica, sericite, aluminum silicate, magnesium silicate, clay, bentonite, etc.), carbonate (calcium carbonate, magnesium carbonate, etc.), sulfuric acid salt (calcium sulfate, barium sulfate, flake shaped barium sulfate, butterfly shaped barium sulfate, magnesium sulfate, etc.), nitride (boron nitride, etc.), phosphoric acid salt (hydroxyapatite, etc.), oxide (magnesium oxide, alumina, etc.) each used as an extender pigment; oxide (zinc oxide, zirconium oxide, titanium oxide, etc.) used as a white pigment; oxide (cerium oxide, etc.), oxide fine particles (zinc oxide fine particles, titanium oxide fine particles, etc.) each used as a UV scattering agent; oxide (yellow iron oxide, red iron oxide, black iron oxide, chrome oxide, cobalt oxide, etc.), carbide (silicon carbide, etc.), carbon (carbon black, etc.), sulfide (ultramarine blue, etc.), ferrocyanide compound (Prussian blue, etc.) each used as a coloring pigment; and mica titanium, oxychloride bismuth, and the like each used as a pearlescent pigment.

In addition, composite powders of powders used as the above-mentioned pigments, for example, silica coated titanium oxide, mica-coated titanium oxide, and the like, surface-treated powders obtained by a surface treatment, such as silicone treatment, fluorine compound treatment, silane coupling agent treatment, silane treatment, organic titanate treatment, acylated fatty acid treatment (e.g., N-stearoyl-L-glutamic acid treatment), metal soap treatment (e.g., aluminum stearate treatment), oleum treatment, amino acid treatment, and the like, of the above-mentioned powders, for example, silicone-treated talc, silicone-treated mica, silicone-treated sericite, silicone treated titanium oxide, silicone treated red iron oxide, silicone-treated yellow iron oxide, silicone-treated black iron oxide, N-stearoyl-L-glutamic acid-treated titanium oxide, N-stearoyl-L-glutamic acid-treated yellow iron oxide, N-stearoyl-L-glutamic acid-treated red iron oxide, N-stearoyl-L-glutamic acid-treated black iron oxide, aluminum stearate-treated titanium oxide, and the like can also be used.

In the water-in-oil type emulsion cosmetics of the present invention, inorganic pigments subjected to a hydrophobic treatment such as silicone treatment, acylated fatty acid treatment, metal soap treatment, oleum treatment, and the like are more preferably used as the inorganic pigment, since they can be well dispersed on the outer oil phase of the water-in-oil type emulsion cosmetics.

One or more kinds of the above-mentioned pigments can be used, and commercially available products for cosmetics provided by each company can also be used.

The content ($W_e$) of component (e) in the water-in-oil type emulsion cosmetics of the present invention is preferably 0.005 mass % to 30 mass %, more preferably 1 mass % to 20 mass %.

The water-in-oil type emulsion cosmetics of the present invention contain water as component (f). As water, water suitable for the production of cosmetics, for example, purified water such as distilled water, deionized water, and the like can be used.

The content ($W_f$) of water in the water-in-oil type emulsion cosmetics of the present invention is set as an amount with respect to the total amount of the water-in-oil type emulsion cosmetics as 100 mass %.

In the present invention, (g) a hydrophilic or water-soluble additive for cosmetics can be added to water as necessary.

In the water-in-oil type emulsion cosmetics of the present invention, one or more members selected from the group consisting of (g-1) amino acid and a salt thereof, (g-2) aliphatic hydroxycarboxylic acid having 1 to 10 carbon atoms and a salt thereof, (g-3) polyhydric alcohol, and (g-4) betaine is/are preferably contained as the (g) hydrophilic or water-soluble additive for cosmetics.

Examples of the amino acid contained as component (g-1) in the water-in-oil type emulsion cosmetics of the present invention include acidic amino acids such as glutamic acid (2-aminopentanedioic acid), aspartic acid (2-aminobutanedioic acid), and the like; basic amino acids such as arginine (2-amino-5-guanidinopentanoic acid), lysine (2,6-diamino hexanoic acid), histidine (2-amino-3-(1H-imidazol-4-yl) propanoic acid), citrulline (2-amino-5-(carbamoylamino) pentanoic acid), ornithine (2,5-diamino pentanoic acid), and the like; and neutral amino acids such as neutral amino acids having an ethylene group or an alkyl group (e.g., glycine (aminoethanoic acid), alanine (2-aminopropanoic acid), valine (2-amino-3-methylbutanoic acid), leucine (2-amino-4-methylpentanoic acid), isoleucine (2-amino-3-methylpentanoic acid)), neutral amino acids having a hydroxy group (e.g., serine (2-amino-3-hydroxypropanoic acid), threonine (2-amino-3-hydroxybutanoic acid)), neutral amino acids containing sulfur (e.g., cysteine (2-amino-3-mercaptopropanoic acid), methionine (2-amino-4-(methylthio) butanoic acid)), neutral amino acids having an amide group (e.g., asparagine (2-amino-3-carbamoylpropanoic acid), glutamine (2-amino-4-carbamoylbutanoic acid)), neutral amino acids having an imino group (e.g., proline (pyrrolidine-2-carboxylic acid)), neutral amino acids having an aromatic group (e.g., phenylalanine (2-amino-3-phenylpropanoic acid), tyrosine (2-amino-3-(4-hydroxyphenyl)propanoic acid), tryptophan (2-amino-3-(1H-indol-3-yl)propanoic acid)), and the like.

Any of the D-form, L-form, and DL-form of the above-mentioned amino acids can be used. L-form and DL-form are preferably used, and L-form is more preferably used.

The salt of the above-mentioned amino acid is not particularly limited as long as it is a pharmaceutically acceptable salt and is used in a composition for skin. Examples thereof include acid addition salts and salts with bases.

Specifically, salts with inorganic bases, organic bases, inorganic acids, and organic acids, and salts with amino acids can be mentioned.

Examples of the salts with inorganic bases include salts with alkali metals such as lithium, sodium, potassium, and the like, salts with alkaline earth metals such as magnesium, calcium, and the like, ammonium salts, and the like.

Examples of the salts with organic bases include salts with alkanol amines such as mono ethanolamine, diethanolamine, triethanolamine, and the like, salt with heterocyclic amines such as morpholine, piperidine, and the like, and the like.

Examples of the salts with inorganic acids include salts with hydrohalic acid (hydrochloric acid, hydrobromic acid, hydroiodic acid, etc.), sulfuric acid, nitric acid, phosphoric acid, and the like.

Examples of the salts with organic acids include salts with monocarboxylic acids such as formic acid, acetic acid, propanoic acid, and the like; salts with saturated dicarboxylic acids such as oxalic acid, malonic acid, succinic acid, and the like; salts with unsaturated dicarboxylic acids such as maleic acid, fumaric acid, and the like; salts with tricarboxylic acids such as aconitic acid and the like; salts with keto acids such as α-ketoglutaric acid and the like, and the like.

Examples of the salts with amino acids include salts with aliphatic amino acids such as alanine and the like; salts with aromatic amino acids such as tyrosine and the like; salts with basic amino acids such as lysine and the like; salts with acidic amino acids such as aspartic acid, glutamic acid, and the like, and the like.

The above-mentioned salts may be each a hydrate (hydrate salt), and examples of such hydrate include 1 hydrate to 6 hydrate.

In the present invention, the above-mentioned acidic amino acids are preferably used in the form of free forms and alkali metal salts such as sodium salt and potassium salt; the basic amino acids are preferably used in the form of free forms and acid addition salts such as hydrochlorides; and neutral amino acids are preferably used in the form of free forms.

The above-mentioned acidic amino acids and salts thereof, basic amino acids and salts thereof, and neutral amino acids and salts thereof to be used may be all extracted and purified from naturally occurring animals and plants, or obtained by chemical synthesis method, fermentation method, enzyme method, or gene recombinant method. Alternatively, commercially available products provided by each company may also be used.

As the amino acid and a salt thereof that may be contained as component (g-1) in the water-in-oil type emulsion cosmetics of the present invention, pyrrolidonecarboxylic acid which is an amino acid in which the carboxyl group and amino group of glutamic acid undergo an intramolecular condensation reaction to form a lactam, and a salt thereof may also be used preferably.

Any of the D-form, L-form, and DL-form of pyrrolidonecarboxylic acid can be used. L-form and DL-form are preferably used.

As the salts of pyrrolidonecarboxylic acid, alkali metal salts such as lithium salt, sodium salt, potassium salt, and the like; zinc salt, and the like can be mentioned, and sodium salt and zinc salt are preferably used.

Pyrrolidonecarboxylic acid and a salt thereof to be used may be produced by chemical synthesis method, enzyme method, or gene recombinant method. Alternatively, commercially available products provided by each company may also be used.

As component (g-1) in the present invention, one kind may be selected from the group consisting of acidic amino acid, basic amino acid, neutral amino acid, and salts thereof, and pyrrolidonecarboxylic acid and a salt thereof mentioned above, and used alone, or two or more kinds may be selected and used in combination.

The content ($W_{g-1}$) of the component (g-1) in the water-in-oil type emulsion cosmetics of the present invention is preferably 0.03 mass % to 1.8 mass %, more preferably 0.08 mass % to 1 mass %.

When an amino acid salt is contained as component (g-1), the content thereof is shown by a content of a free form thereof.

Since the water-in-oil type emulsion cosmetics of the present invention can be imparted with a good moist feeling and a skin conditioning effect, one or more members selected from the group consisting of pyrrolidonecarboxylic acids such as pyrrolidonecarboxylic acid, sodium pyrrolidonecarboxylate, zinc pyrrolidonecarboxylate, and the like, and salts thereof, and arginine, which is an amino acid constituting a natural moisturizing factor, and a salt thereof is/are preferably used as component (g-1).

In addition to arginine, one or more members selected from the group consisting of aspartic acid, asparagine, glutamic acid, glutamine, lysine, histidine, threonine, serine, proline, glycine, alanine, valine, leucine, phenylalanine, tyrosine, citrulline, and ornithine, which are amino acids constituting natural moisturizing factors, and salts thereof can be preferably used.

From the aspects of improving moist feeling and emulsion stability, the water-in-oil type emulsion cosmetics of the present invention may preferably contain one or more members selected from the group consisting of (g-2) aliphatic hydroxycarboxylic acid having 1 to 10 carbon atoms and a salt thereof, (g-3) polyhydric alcohol, and (g-4) betaine, as the (g) hydrophilic or water-soluble additive for cosmetics.

The aliphatic hydroxycarboxylic acid having 1 to 10 carbon atoms that may be contained as component (g-2) is an acyclic or cyclic carboxylic acid having 1 to 10 carbon atoms and having one or more hydroxy groups.

Examples of such aliphatic hydroxycarboxylic acid include acyclic hydroxycarboxylic acids such as glycolic acid, lactic acid, tartronic acid, glyceric acid, hydroxybutyric acid (2-hydroxybutyric acid, 3-hydroxybutyric acid, 4-hydroxybutyric acid), malic acid, tartaric acid, citramalic acid, citric acid, isocitric acid, leucic acid, mevalonic acid, pantoic acid, pantothenic acid, and the like; and cyclic hydroxycarboxylic acids such as quinic acid, shikimic acid, and the like.

From the aspect of emulsion stability improving effect, an acyclic hydroxycarboxylic acid having 1 to 10 carbon atoms is preferred, acyclic hydroxycarboxylic acids having 2 to 6 carbon atoms such as lactic acid, tartronic acid, glyceric acid, hydroxybutyric acid (2-hydroxybutyric acid, 3-hydroxybutyric acid, 4-hydroxybutyric acid), malic acid, tartaric acid, citramalic acid, citric acid, isocitric acid, leucic acid, mevalonic acid, pantoic acid, and the like are more preferred, and citric acid is particularly preferred.

In the present invention, a salt of the above-mentioned hydroxycarboxylic acid can also be used as component (g-2).

Such salt is not particularly limited as long as it is a pharmaceutically acceptable salt used for skin compositions. Examples thereof include salts with inorganic base such as alkali metal salts such as lithium salt, sodium salt, potassium salt, and the like; alkaline earth metal salts such as magnesium salt, calcium salt, and the like; ammonium salt, and the like, salts with organic base such as alkanol amine salts such as mono ethanolamine salt, diethanolamine salt, triethanolamine salt, and the like; salts with heterocyclic amine such as morpholine salt, piperidine salt, and the like; salts with basic amino acid such as arginine salt, lysine salt, histidine salt, and the like. An alkali metal salt such as sodium salt or the like is preferably used.

In the present invention, the above-mentioned aliphatic hydroxycarboxylic acid having 1 to 10 carbon atoms and a salt thereof to be used may be extracted and purified from animals and plants abundantly containing them, or obtained by chemical synthesis method, fermentation method, or gene recombinant method. Alternatively, commercially available products provided by each company may also be used.

In the water-in-oil type emulsion cosmetics of the present invention, one kind of the above-mentioned aliphatic hydroxycarboxylic acid having 1 to 10 carbon atoms and a salt thereof may be used alone, or two or more kinds thereof may be selected and used in combination.

The content ($W_{g-2}$) of component (g-2) in the water-in-oil type emulsion cosmetics of the present invention is preferably 0.003 mass % to 0.2 mass %, more preferably 0.009 mass % to 0.04 mass %.

When a salt of aliphatic hydroxycarboxylic acid having 1 to 10 carbon atoms is contained as component (g-2), the above-mentioned content is shown as a content converted to that of a free form.

Examples of the polyhydric alcohol contained as component (g-3) include divalent alcohols such as propylene glycol, dipropylene glycol, 1,3-butyleneglycol, 1,2-pentanediol (pentylene glycol), and the like, trivalent alcohols such as glycerol and the like, sugar alcohols such as xylitol, sorbitol, maltitol, mannitol, and the like, and the like. One kind thereof may be used alone, or two or more kinds thereof may be used in combination.

For the purpose of the present invention, glycerol, 1,3-butyleneglycol and the like are preferably used, and 1,3-butyleneglycol and the like are more preferably used as polyhydric alcohol.

As polyhydric alcohol, commercially available products for cosmetics provided by each company can also be used.

The content ($W_{g-3}$) of component (g-3) in the water-in-oil type emulsion cosmetics of the present invention is preferably 0.019 mass % to 6 mass %, more preferably 0.04 mass % to 5.2 mass %.

Betaine contained as component (g-4) is a compound having a positive charge and a negative charge at non-adjacent positions in the same molecule, in which dissociable hydrogen is not bonded to an atom with positive charge, and the molecule as a whole has no charge. Trimethylglycine, carnitine, proline betaine, and the like are exemplified, and trimethylglycine is preferably used.

As betaine, commercially available products, for cosmetics provided by each company can be used.

The content ($W_{g-4}$) of component (g-4) in the water-in-oil type emulsion cosmetics of the present invention is preferably 0.01 mass % to 0.8 mass %, more preferably 0.03 mass % to 0.2 mass %.

In the water-in-oil type emulsion cosmetics of the present invention, hydrophilic or water-soluble general additives can be added as necessary as (g) hydrophilic or water-soluble additive for cosmetics, in addition to the above-mentioned component (g-1) to component (g-4).

Examples of such additives include suspending agents such as alginic acid propylene glycol ester, dioctyl sodium sulfosuccinate, soybean lecithin, povidone, and the like; thickening agents such as carboxyvinyl polymer, sodium polyacrylate, xanthan gum, carboxymethylcellulose, hydroxypropylcellulose, (partially hydrolyzed) poly(vinyl alcohol), and the like; pH adjusters such as hydrochloric acid, phosphoric acid, succinic acid, sodium hydroxide, potassium hydroxide, sodium acetate, sodium hydrogenphosphate, 1-amino-2-propanol, and the like; stabilizers such as disodium ethylenediaminetetraacetate, polyoxyethylene polyoxypropylene glycol, and the like; antioxidants such as ascorbic acid, sodium erythorbate, and the like; antiseptics such as sorbic acid, sodium dehydroacetate, methyl parahydroxybenzoate, phenoxyethanol, and the like; hydrophilic or water-soluble dyes such as Red No. 2, Yellow No. 3, Blue No. 1, anthocyanin, carthamins yellow, and the like; hydrophilic or water-soluble flavors such as phenethyl alcohol, lavender extract, and the like, and the like. One or more kinds thereof may be used as necessary.

The water-in-oil type emulsion cosmetics of the present invention can be produced according to a general method for producing a water-in-oil type emulsion.

For example, component (a) is added to (f) water together with component (g), which is added as necessary, and mixed to form a uniform aqueous phase. On the other hand, component (D) is added to component (C), and mixed to form a uniform oil phase. The aforementioned aqueous phase and oil phase are respectively heated to 75° C. to 85° C., and the aqueous phase is added to the oil phase with stirring to achieve emulsification.

The component (b) and component (e) are dispersed in the water phase or the oil phase as appropriate according to the affinity thereof for water or oil and added.

Among the lipophilic or oil-soluble cosmetic additives added as component (c) and the hydrophilic or water-soluble cosmetic additives added as component (g), components with low heat stability can be added and mixed after emulsification and cooling.

Dispersing of component (b) and component (e) in the aqueous phase or the oil phase, and emulsification treatment can be performed well using a stirring machine such as disper or homo disper, an emulsification equipment such as homomixer, homogenizer, or colloid mill, or the like.

When producing the water-in-oil type emulsion cosmetics of the present invention, the above-mentioned component (a) and components (g-1) to (g-4) can also be used by mixing and dissolving in advance in a portion of water.

The water-in-oil type emulsion cosmetics of the present invention can be provided as skin cosmetics such as milky lotion, serum, cream, facial mask, and the like; foundation primers such as make up base lotion, makeup base cream, and the like; makeup cosmetics such as milky liquid foundation, creamy foundation, creamy eye color, creamy cheek color, creamy eyeliner, creamy mascara, and the like; body cosmetics such as body lotion, body cream, and the like;

suntan cosmetics such as tanning lotion and the like; sunscreen cosmetics such as sunscreen lotion, sunscreen cream, and the like, and the like.

From the aspects of emulsion stability, dispersion stability of pigment, feeling of use, and the like, the water-in-oil type emulsion cosmetics of the present invention preferably has a viscosity of not less than 10 Pa·s, more preferably not less than 30 Pa·s, at 25° C. From the aspects of easy application to the skin, spreadability, and the like, the viscosity at 25° C. is preferably not more than 1,000 Pa·s, more preferably not more than 500 Pa·s.

The viscosity of the water-in-oil type emulsion cosmetics of the present invention can be calculated from the measurement value after rotating for 30 seconds at a rotation speed of 1.5 rpm to 12 rpm at 25° C. using a Brookfield type viscometer (manufactured by TOKYO KEIKI INC., DV L-B, etc.), Rotor No. 4.

The water-in-oil type emulsion cosmetics of the present invention contain pigments, afford good makeup effects, that is, color development, covering power, and soft focus effect of cosmetics, further have a good moist feeling, and are superior in emulsion stability and pigment dispersibility.

Other features of the invention will become apparent in the course of the following descriptions of exemplary embodiments which are given for illustration of the invention and are not intended to be limiting thereof.

EXAMPLES

Examples 1-3, Comparative Examples 1-5. Water-In-Oil Type Emulsion Cosmetics According to the formulations shown in Table 1, component (a) and component (g) were added to component (f), and they were uniformly mixed and heated to 80° C. to give an aqueous phase. Component (d) was added to component (c), and they were uniformly mixed and heated to 80° C. Component (b) and component (e) mixed in advance were added to the aforementioned mixture of component (d) and component (c), dispersed therein, and heated to 80° C. to give an oil phase. To the aforementioned oil phase was gradually added the aforementioned aqueous phase and the mixture was emulsified to prepare liquid water-in-oil type emulsion cosmetics of Examples 1 to 3 and Comparative Examples 1 to 5.

As component (a), "AQUADEW SPA-30B" (weight average molecular weight of sodium polyaspartate=3,000 to 5,000) (Ajinomoto Co., Inc.) was used. The content of component (a) in the table shows the net content of sodium polyaspartate. As component (b), completely spherical nylon-12 powder ("SP-500", manufactured by Toray Industries, Inc.) with a volume-based average particle size of 5 μm as measured by the laser diffraction/scattering method was used. As component (c), component (d), component (e), and component (g), commercially available products for cosmetics were used. As component (f), purified water was used.

The content of 1,3-butyleneglycol in the table includes the content derived from "AQUADEW SPA-30B" (Ajinomoto Co., Inc.), and disodium ethylenediaminetetraacetate·dihydrate is a component derived from "AQUADEW SPA-30B" (Ajinomoto Co., Inc.).

With regard to the water-in-oil type emulsion cosmetics of Examples 1-3 and Comparative Examples 1-5, the viscosity at 25° C. was measured, and the color development (lightness) of cosmetics, covering power, soft focus effect, moist feeling, emulsion stability, and pigment dispersion stability were evaluated as shown below. The evaluation results are also shown in Table 1.

(1) Viscosity at 25° C.

The viscosity was calculated from the measured value obtained after rotation using a Brookfield type viscometer ("DV L-B", TOKYO KEIKI INC.) at 25° C. (rotor No. 4, rotating speed 1.5 rpm to 12 rpm) for 30 seconds.

(2) Color Development (Lightness) of Cosmetics

With regard to the respective emulsion cosmetics of Examples and Comparative Examples, the L value, a value, and b value were measured under the condition of the reflection measurement, ϕ=10 mm, immediately after preparation and by using a colorimetric color difference meter ZE6000 (NIPPON DENSHOKU INDUSTRIES Co., Ltd.), and the measured L values were evaluated according to the following evaluation criteria.

Evaluation Criteria

- L value is 65 or above; A
- L value is 63 or above and less than 65; B
- L value is 61 or above and less than 63; C
- L value is less than 61; D (3) Covering Power 0.1 g of each of the emulsion cosmetics of Examples and Comparative Examples was taken, spread evenly on a 2.5 cm×6 cm artificial leather (black) with a bar coater, and visually evaluated according to the following evaluation criteria.

Evaluation Criteria

- having high covering power; A
- having covering power; B
- having some covering power; C
- having no covering power; D (4) Soft Focus Effect 0.1 g of each of the emulsion cosmetics of Examples and Comparative Examples was taken, spread evenly on a 2.5 cm×6 cm artificial leather (black) with a bar coater. Using a goniophotometer GP-200 (Murakami Color Research Laboratory Co., Ltd.), the reflectance was measured under the following measurement conditions, and an index value showing psychological gloss was calculated by dividing the light intensity at the light receiving angle=45° by the light intensity at the light receiving angle=0°.

Measurement Conditions

- (i) incident angle: −45°
- (ii) receiving angle: variable angle (−90° to 90°)
- (iii) COASE: 05
- (iv) H.V.: 03
- (v) VS1: 2.0
- (vi) VS3: 4.0

From the calculated index value, the soft focus effect was evaluated according to the following evaluation criteria.

Evaluation Criteria

- Index value showing psychological gloss is less than 1.6; A
- Index value showing psychological gloss is 1.6 or more and less than 1.9; B
- Index value showing psychological gloss is 1.9 or more and less than 2.2; C
- Index value showing psychological gloss is 2.2 or more; D (5) Moist Feeling About 0.1 g of each of the emulsion cosmetics of Examples and Comparative Examples was applied to the back of the hands of the panelists, and the moist feeling was evaluated according to the following evaluation criteria.

Evaluation Criteria having high moist feeling; A having moist feeling; B having some moist feeling; C having no moist feeling; D (6) Emulsion Stability As an acceleration test corresponding to storage for one year, about 1 g of each emulsion cosmetic of Examples and Comparative Examples was placed in a microtube and weighed precisely to determine the weight of each emulsion cosmetic, centrifuged at 15,000 rpm for 30 min at 25° C. in a compact centrifugal separator (inner diameter=7.18 cm), and the supernatant liquid after syneresis was collected with a micropipette and weighed. The weight of the aforementioned supernatant liquid was divided by the weight of the emulsion cosmetic subjected to the test to obtain the rate of syneresis (%), and the emulsion stability was evaluated according to the following evaluation criteria.

Evaluation Criteria

Rate of syneresis is less than 2.5%; A

Rate of syneresis is 2.5% or more and less than 5.0%; B

Rate of syneresis is 5.0% or more and less than 10%; C

Rate of syneresis is 10% or more; D (7) Dispersion Stability of Pigment

As an acceleration test corresponding to storage for one year, about 1 g of each emulsion cosmetic of Examples and Comparative Examples was placed in a microtube, centrifuged at 15,000 rpm for 30 min at 25° C. in a compact centrifugal separator (inner diameter=7.18 cm), the state (color) of the emulsion cosmetic in the microtube was observed, and the dispersion stability of the pigment was evaluated according to the following evaluation criteria.

Evaluation Criteria

Color is uniform from top to bottom in the microtube; A

Color unevenness is seen on the top or bottom of the microtube; B

Color is vaguely divided between the top and bottom of the microtube (color border not clear); C Color is clearly separated between the top and bottom of the microtube (color border clearly visible); D

| | component | Ex. 1 | Ex. 2 | Ex. 3 | Comp. Ex. 1 | Comp. Ex. 2 | Comp. Ex. 3 | Comp. Ex. 4 | Comp. Ex. 5 |
|---|---|---|---|---|---|---|---|---|---|
| (a) | sodium polyaspartate | 0.9 (0.76) | 0.45 (0.38) | 0.09 (0.076) | — | 0.9 (0.76) | 0.45 (0.38) | 0.09 (0.076) | — |
| (b) | nylon-12 | 0.1 | 0.1 | 0.1 | — | — | — | — | 0.1 |
| (c) | decamethylcyclopentasiloxane | 10.0 | 10.0 | 10.0 | 10.0 | 10.0 | 10.0 | 10.0 | 10.0 |
| | liquid paraffin | 5.0 | 5.0 | 5.0 | 5.0 | 5.0 | 5.0 | 5.0 | 5.0 |
| | 2-ethylhexyl methoxycinnamate | 5.0 | 5.0 | 5.0 | 5.0 | 5.0 | 5.0 | 5.0 | 5.0 |
| | glyceryl tribehenate | 2.0 | 2.0 | 2.0 | 2.0 | 2.0 | 2.0 | 2.0 | 2.0 |
| (d) | sorbitan monoisostearate (HLB value = 5.0) | 4.0 | 4.0 | 4.0 | 4.0 | 4.0 | 4.0 | 4.0 | 4.0 |
| (e) | dimethylpolysiloxane-treated alumina, silica-coated titanium oxide | 8.0 | 8.0 | 8.0 | 8.0 | 8.0 | 8.0 | 8.0 | 8.0 |
| | silica-coated yellow iron oxide treated with dimethylpolysiloxane | 1.0 | 0.1 | 0.1 | 0.1 | 0.1 | 0.1 | 0.1 | 0.1 |
| | silica-coated red iron oxide treated with dimethylpolysiloxane | 0.2 | 2.0 | 2.0 | 2.0 | 2.0 | 2.0 | 2.0 | 2.0 |
| | silica-coated black iron oxide treated with dimethylpolysiloxane | 0.1 | 0.1 | 0.1 | 0.1 | 0.1 | 0.1 | 0.1 | 0.1 |
| (f) | water | balance | balance | balance | balance | balance | balance | balance | balance |
| (g) | 1,3-butyleneglycol | 5.0 | 5.0 | 5.0 | 5.0 | 5.0 | 5.0 | 5.0 | 5.0 |
| | disodium ethylenediaminetetraacetate dihydrate | 0.003 | 0.0015 | 0.0003 | — | 0.003 | 0.0015 | 0.0003 | — |
| | methyl p-hydroxybenzoate | 0.1 | 0.1 | 0.1 | 0.1 | 0.1 | 0.1 | 0.1 | 0.1 |
| total amount | | 100 | 100 | 100 | 100 | 100 | 100 | 100 | 100 |
| viscosity (Pa · s) | | 193.9 | 104.4 | 177.1 | 36.8 | 389.1 | 128.1 | 275.1 | 25.6 |
| color development of cosmetics (lightness) | | A | B | B | B | A | B | B | C |
| covering power | | A | A | B | B | B | D | C | C |
| soft focus effect | | B | C | B | B | D | C | B | B |
| moist feeling | | B | B | C | D | B | C | D | D |
| emulsion stability | | A | B | B | D | A | C | B | D |
| dispersion stability of pigment | | A | B | B | D | B | C | B | D |

*; In table, numerical value corresponding to each component shows the content (mass %) of the component, and "—" shows that the component is not contained. Numerical value in parenthesis shows value converted to free form.

As shown in Table 1, each water-in-oil emulsion cosmetic of Examples 1 to 3 containing (a) 0.09% mass % to 0.9 mass % of sodium polyaspartate (0.076 mass % to 0.76 mass % in terms of free form), and (b) nylon-12 as spherical powder obtained an evaluation of "C" or higher in any evaluation item.

In contrast, the water-in-oil type emulsion cosmetic of Comparative Example 1 not containing (a) sodium polyaspartate and (b) nylon-12, and the emulsion cosmetic of Comparative Example 5 containing (b) nylon-12 but not containing (a) sodium polyaspartate obtained an evaluation of "D" for moist feeling, emulsion stability, and pigment dispersion stability. In addition, each water-in-oil type emulsion cosmetic of Comparative Examples 2 to 4 containing (a) 0.09% mass % to 0.9 mass % of sodium polyaspartate (0.076 mass % to 0.76 mass % in terms of free form) but not containing (b) nylon-12 obtained an evaluation of "D" for soft focus effect, covering power, and moist feeling.

Each water-in-oil type emulsion cosmetic of Examples 1 to 3 showed appropriate viscosity of about 100 Pa·s to 200 Pa·s at 25° C.

From the above results, it was suggested that (a) polyaspartic acid or a salt thereof and (b) spherical powder must be used together in order to obtain a water-in-oil type emulsion cosmetic containing (e) pigment and superior in the color development, covering power, makeup effects such as soft focus effect and the like and moist feeling, and emulsion stability and pigment dispersion stability.

Examples 4-10. Examination of Influence of the Kind of Spherical Powder

By a method similar to that in Example 1 except that nylon-12 as component (b) was changed to the spherical powder shown in Table 2, water-in-oil type emulsion cosmetics were prepared and used as Examples 4 to 10.

As the spherical powder shown in Table 2, a commercially available product provided for cosmetics was used.

With regard to the respective water-in-oil type emulsion cosmetics of Examples 4 to 10, in the same manner as in the water-in-oil type emulsion cosmetics of Examples 1 to 3 and Comparative Example 1 to 5, the viscosity was measured and the color development (lightness) of cosmetics, covering power, soft focus effect, moist feeling, emulsion stability, and pigment dispersion stability were evaluated. The results are also shown in Table 2.

As shown in Table 2, the water-in-oil type emulsion cosmetics of Examples 4 to 6 containing spherical silicic anhydride as the (b) spherical powder, the water-in-oil type emulsion cosmetics of Examples 7 to 9 containing spherical silicone powder as the (b) spherical powder, and the water-in-oil type emulsion cosmetics of Example 10 containing spherical cellulose as the (b) spherical powder obtained a good evaluation of "C" or higher in all evaluation items of the color development (lightness) of cosmetics, covering power, soft focus effect, moist feeling, emulsion stability, and pigment dispersion stability.

Each water-in-oil type emulsion cosmetic of Examples 4 to 10 showed appropriate viscosity of about 300 Pas to 400 Pa·s at 25° C.

From the above results, it was suggested that a water-in-oil type emulsion cosmetic containing (a) polyaspartic acid or a salt thereof and (b) spherical powder shows good makeup effects and moist feeling, as well as good emulsion stability and pigment dispersibility irrespective of the kind of the (b) spherical powder.

Examples 11-15. Examination of Influence of the Kind of Oily Component

According to the formulation shown in Table 3 and in the same manner as in the water-in-oil type emulsion cosmetics of the above-mentioned Examples 1 to 3, the water-in-oil type emulsion cosmetics of Examples 11 to 15 were prepared. As the (c) oily component in Table 3, a commercially available product provided for cosmetics was used.

With regard to the respective water-in-oil type emulsion cosmetics of Examples 11 to 15, in the same manner as in the water-in-oil type emulsion cosmetics of Examples 1 to 3 and Comparative Example 1 to 5, the viscosity was measured and the color development (lightness) of cosmetics, covering power, soft focus effect, moist feeling, emulsion stability, and pigment dispersion stability were evaluated. The results are also shown in Table 3.

| Ex. | (b) spherical powder | volume-based average particle size (μm) | viscosity (Pa · s) | color development (lightness) of cosmetics | covering power | soft focus effect | moist feeling | emulsion stability | pigment dispersion stability |
|---|---|---|---|---|---|---|---|---|---|
| 4 | spherical silicic anhydride | 4 | 372.7 | A | C | B | B | A | B |
| 5 | spherical silicic anhydride | 20 | 381.4 | B | B | B | B | A | B |
| 6 | spherical silicic anhydride | 9 | 397.4 | B | B | A | B | A | B |
| 7 | spherical silicone; (diphenyldimethylpolysiloxane/vinyldiphenyldimethyl-polysiloxane/silsesquioxane) crosslinked polymer | 5 | 288.6 | B | A | A | B | A | B |
| 8 | spherical silicone; polymethyl silsesquioxane | 6 | 316.5 | A | B | A | C | A | B |
| 9 | spherical silicone; polymethyl silsesquioxane | 0.8 | 390.8 | A | A | B | B | A | B |
| 10 | spherical cellulose | 5 | 354.5 | A | B | A | B | A | A |

TABLE 3

| | component | Ex. 11 | Ex. 12 | Ex. 13 | Ex. 14 | Ex. 15 |
|---|---|---|---|---|---|---|
| (a) | sodium polyaspartate | 0.9 (0.76) | 0.9 (0.76) | 0.9 (0.76) | 0.9 (0.76) | 0.9 (0.76) |
| (b) | nylon-12 | 1.0 | 1.0 | 1.0 | 1.0 | 1.0 |
| (c) | decamethylcyclopentasiloxane | — | 10.0 | 10.0 | 10.0 | 10.0 |
| | dimethylpolysiloxane | 10.0 | — | — | — | — |
| | liquid paraffin | 5.0 | — | 5.0 | 5.0 | 5.0 |
| | squalane | — | 5.0 | — | — | — |
| | 2-ethylhexyl methoxycinnamate | 5.0 | 5.0 | — | — | 5.0 |
| | cetyl 2-ethylhexanoate | — | — | 5.0 | — | — |
| | di(phytosteryl/octyldodecyl) N-lauroyl-L-glutamate | — | — | — | 5.0 | — |
| | glyceryl tribehenate | 2.0 | 2.0 | 2.0 | 2.0 | — |
| | microcrystalline wax | — | — | — | — | 2.0 |
| (d) | sorbitan monoisostearate (HLB value = 5.0) | 4.0 | 4.0 | 4.0 | 4.0 | 4.0 |
| (e) | dimethylpolysiloxane-treated alumina, silica-coated titanium oxide | 8.0 | 8.0 | 8.0 | 8.0 | 8.0 |
| | silica-coated yellow iron oxide treated with dimethylpolysiloxane | 1.0 | 1.0 | 1.0 | 1.0 | 1.0 |
| | silica-coated red iron oxide treated with dimethylpolysiloxane | 0.2 | 0.2 | 0.2 | 0.2 | 0.2 |
| | silica-coated black iron oxide treated with dimethylpolysiloxane | 0.1 | 0.1 | 0.1 | 0.1 | 0.1 |
| (f) | water | balance | balance | balance | balance | balance |
| (g) | 1,3-butyleneglycol | 5.0 | 5.0 | 5.0 | 5.0 | 5.0 |
| | disodium ethylenediaminetetraacetate•dihydrate | 0.003 | 0.003 | 0.003 | 0.003 | 0.003 |
| | methyl p-hydroxybenzoate | 0.1 | 0.1 | 0.1 | 0.1 | 0.1 |
| total amount | | 100 | 100 | 100 | 100 | 100 |
| viscosity (Pa · s) | | 67.0 | 95.3 | 33.2 | 375.6 | 30.5 |
| color development (lightness) of cosmetics | | B | B | B | B | B |
| covering power | | B | B | C | A | C |
| soft focus effect | | B | A | C | B | C |
| moist feeling | | B | B | B | A | B |
| emulsion stability | | C | A | C | A | C |
| pigment dispersion stability | | C | C | C | B | C |

*; In table, numerical value corresponding to each component shows the content (mass %) of the component, and "—" shows that the component is not contained. Numerical value in parenthesis shows value converted to free form.

As shown in Table 3, the water-in-oil type emulsion cosmetics of Examples 11 to 15 of the present invention obtained a good evaluation of "C" or higher in all evaluation items of the color development (lightness) of cosmetics, covering power, soft focus effect, moist feeling, emulsion stability, and pigment dispersion stability, irrespective of the kind of the contained oily component.

Each water-in-oil type emulsion cosmetic of Examples 11 to 15 showed appropriate viscosity of about 30 Pa·s to 400 Pa·s at 25° C.

From the above results, it was suggested that the water-in-oil type emulsion cosmetics of the present invention affords good makeup effects and moist feeling, as well as good emulsion stability and pigment dispersibility irrespective of the kind of the contained oily component.

Example 16. Examination of Influence of the Kind of Emulsifier

In the same manner as in the above-mentioned Example 1 except that the emulsifier was changed to a silicone-based surfactant, polyoxyethylene (10E.O.)·polyoxypropylene (1P.O.) modified cetyl dimethylpolysiloxane·dimethylpolysiloxane copolymer (HLB value=4 to 6), the water-in-oil type emulsion cosmetic of Example 16 was prepared. As the aforementioned silicone-based surfactant, a commercially available product provided for cosmetics was used.

With regard to the water-in-oil type emulsion cosmetic of Example 16, in the same manner as in the water-in-oil type emulsion cosmetics of Examples 1 to 3 and Comparative Example 1 to 5, the viscosity was measured and the color development (lightness) of cosmetics, covering power, soft focus effect, moist feeling, emulsion stability, and pigment dispersion stability were evaluated. The results are also shown in Table 4.

TABLE 4

| evaluation item | Example 16 |
|---|---|
| viscosity (Pa · s) | 85.6 |
| color development (lightness) of cosmetics | A |
| covering power | B |
| soft focus effect | B |
| moist feeling | B |
| emulsion stability | A |
| pigment dispersion stability | B |

As shown in Table 4, a good evaluation of "A" or "B" was obtained in all evaluation items of the color development (lightness) of cosmetics, covering power, soft focus effect, moist feeling, emulsion stability, and pigment dispersion stability, even when a silicone-based surfactant was used as component (d), and showed appropriate viscosity of 85.6 Pa·s at 25° C.

From the above results, it was suggested that silicone-based surfactants can also be used preferably as the component (d) in the preparation of the water-in-oil type emulsion cosmetics of the present invention.

Example 17. Examination of Influence of the Kind of Pigment

According to the formulation shown in Table 5 and in the same manner as in the water-in-oil type emulsion cosmetics of the above-mentioned Examples 1 to 3, the water-in-oil type emulsion cosmetic of Example 17 was prepared. As the pigment in Table 5, a commercially available product provided for cosmetics was used.

With regard to the water-in-oil type emulsion cosmetic of Example 17, in the same manner as in the water-in-oil type emulsion cosmetics of Examples 1 to 3 and Comparative Example 1 to 5, the viscosity was measured and the color development (lightness) of cosmetics, covering power, soft focus effect, moist feeling, emulsion stability, and pigment dispersion stability were evaluated. The results are also shown together in Table 5.

TABLE 5

| component | | Example 17 |
|---|---|---|
| (a) | sodium polyaspartate | 0.9 (0.76) |
| (b) | nylon-12 | 1.0 |
| (c) | decamethylcyclopentasiloxane | 10.0 |
| | liquid paraffin | 5.0 |
| | 2-ethylhexyl methoxycinnamate | 5.0 |
| | glyceryl tribehenate | 2.0 |
| (d) | sorbitan monoisostearate (HLB value = 5.0) | 4.0 |
| (e) | aluminum hydroxide-coated titanium oxide treated with disodium N-stearoyl-L-glutamate | 8.0 |
| | aluminum hydroxide-coated yellow iron oxide treated with disodium N-stearoyl-L-glutamate | 1.0 |
| | aluminum hydroxide-coated red iron oxide treated with disodium N-stearoyl-L-glutamate | 0.2 |
| | aluminum hydroxide-coated black iron oxide treated with disodium N-stearoyl-L-glutamate | 0.1 |
| (f) | water | balance |
| (g) | 1,3-butyleneglycol | 5.0 |
| | disodium ethylenediaminetetraacetate•dihydrate | 0.003 |
| | methyl p-hydroxybenzoate | 0.1 |
| total amount | | 100 |
| viscosity (Pa · s) | | 231.1 |
| color development (lightness) of cosmetics | | B |
| covering power | | B |
| soft focus effect | | A |
| moist feeling | | A |
| emulsion stability | | B |
| pigment dispersion stability | | A |

*; In table, numerical value corresponding to each component shows the content (mass %) of the component.

As shown in Table 5, a good evaluation of "A" or "B" was obtained in all evaluation items of the color development (lightness) of cosmetics, covering power, soft focus effect, moist feeling, emulsion stability, and pigment dispersion stability, even when a hydrophobized pigment obtained by a surface treatment of aluminum hydroxide-coated titanium oxide, aluminum hydroxide-coated yellow iron oxide, aluminum hydroxide-coated red iron oxide, or aluminum hydroxide-coated black iron oxide, with disodium N-stearoyl-L-glutamate was used as the pigment, and showed appropriate viscosity of 231.1 Pa·s at 25° C.

From the above results, it was suggested that the water-in-oil type emulsion cosmetics of the present invention afford good makeup effects and moist feeling even when a different kind of a hydrophobized pigment is used, and are also superior in the emulsion stability and pigment dispersion stability.

Examples 18 to 21. Examination of Influence of the Kind of Hydrophilic or Water-Soluble Additive for Cosmetics According to the formulation shown in Table 6 and in the same manner as in the water-in-oil type emulsion cosmetics of the above-mentioned Examples 1 to 3, the water-in-oil type emulsion cosmetics of Examples 18 to 21 were prepared. As the hydrophilic or water-soluble additive for cosmetics in Table 6, a commercially available product provided for cosmetics was used.

With regard to the respective water-in-oil type emulsion cosmetics of Examples 18 to 21, in the same manner as in the water-in-oil type emulsion cosmetics of Examples 1 to 3 and Comparative Example 1 to 5, the viscosity was measured and the color development (lightness) of cosmetics, covering power, soft focus effect, moist feeling, emulsion stability, and pigment dispersion stability were evaluated. The results are also shown together in Table 6.

TABLE 6

| component | | Ex. 18 | Ex. 19 | Ex. 20 | Ex. 21 |
|---|---|---|---|---|---|
| (a) | sodium polyaspartate | 0.9 (0.76) | 0.9 (0.76) | 0.9 (0.76) | 0.2 (0.17) |
| (b) | nylon-12 | 1.0 | 1.0 | 1.0 | 1.0 |
| (c) | decamethylcyclopentasiloxane | 10.0 | 10.0 | 10.0 | 10.0 |
| | liquid paraffin | 5.0 | 5.0 | 5.0 | 5.0 |
| | 2-ethylhexyl methoxycinnamate | 5.0 | 5.0 | 5.0 | 5.0 |
| | glyceryl tribehenate | 2.0 | 2.0 | 2.0 | 2.0 |
| (d) | sorbitan monoisostearate (HLB value = 5.0) | 4.0 | 4.0 | 4.0 | 4.0 |
| (e) | dimethylpolysiloxane-treated alumina, silica-coated titanium oxide | 8.0 | 8.0 | 8.0 | 8.0 |
| | silica-coated yellow iron oxide treated with dimethylpolysiloxane | 1.0 | 1.0 | 1.0 | 1.0 |
| | silica-coated red iron oxide treated with dimethylpolysiloxane | 0.2 | 0.2 | 0.2 | 0.2 |
| | silica-coated black iron oxide treated with dimethylpolysiloxane | 0.1 | 0.1 | 0.1 | 0.1 |
| (f) | water | balance | balance | balance | balance |
| (g) | 1,3-butyleneglycol | 5.0 | 5.0 | 5.0 | 5.20 |
| | sodium pyrrolidonecarboxylate | 1.08 (0.92) | — | — | 0.24 (0.20) |
| | zinc pyrrolidonecarboxylate | — | 0.45 (0.36) | — | 0.10 (0.08) |
| | arginine | — | — | 0.18 | 0.04 |
| | trimethylglycine | — | — | — | 0.15 |
| | trisodium citrate | — | — | — | 0.05 (0.037) |

TABLE 6-continued

| component | Ex. 18 | Ex. 19 | Ex. 20 | Ex. 21 |
|---|---|---|---|---|
| glutamic acid | — | — | — | 0.002 |
| lysine hydrochloride | — | — | — | 0.003 (0.002) |
| serine | — | — | — | 0.015 |
| disodium ethylenediaminetetraacetate•dihydrate | 0.003 | 0.003 | 0.003 | 0.0007 |
| methyl p-hydroxybenzoate | 0.1 | 0.1 | 0.1 | 0.1 |
| total amount | 100 | 100 | 100 | 100 |
| viscosity (Pa · s) | 34.8 | 191.8 | 165.2 | 171.8 |
| color development (lightness) of cosmetics | B | B | B | B |
| covering power | B | B | B | B |
| soft focus effect | A | A | A | C |
| moist feeling | A | A | B | A |
| emulsion stability | C | B | B | B |
| pigment dispersion stability | B | B | B | B |

*; In table, numerical value corresponding to each component shows the content (mass %) of the component, and "—" shows that the component is not contained. Numerical value in parenthesis shows value converted to free form.

As shown in Table 6, the water-in-oil type emulsion cosmetics of Examples 18 and 19 containing a pyrrolidonecarboxylic acid salt as the (g) hydrophilic or water-soluble additive for cosmetics, and the water-in-oil type emulsion cosmetic of Example 20 containing arginine as the (g) hydrophilic or water-soluble additive for cosmetics showed improved soft focus effects and obtained an evaluation of "C" or higher in the emulsion stability and pigment dispersion stability. In addition, the water-in-oil type emulsion cosmetic of Example 21 containing a pyrrolidonecarboxylic acid salt, trimethylglycine, a citric acid salt, amino acids and an amino acid salt as the (g) hydrophilic or water-soluble additive for cosmetics, and containing 0.2 mass % of sodium polyaspartate (0.17 mass % in terms of free form) showed a rather decreasing tendency in the soft focus effect, but evaluated to be superior in the moist feeling and good in emulsion stability and pigment dispersion stability.

The water-in-oil type emulsion cosmetics of Examples 18 to 21 showed appropriate viscosity of about 30 Pa·s to 200 pa·s at 25° C.

From the above results, it was suggested that the soft focus effect may improve in the water-in-oil type emulsion cosmetics of the present invention by adding pyrrolidonecarboxylic acid salt or arginine as the (g) hydrophilic or water-soluble additive for cosmetics.

In addition, it was suggested that the moist feeling may improve in the water-in-oil type emulsion cosmetics of the present invention by adding a pyrrolidonecarboxylic acid salt, trimethylglycine, a citric acid salt, or an amino acid or a salt thereof as the (g) hydrophilic or water-soluble additive for cosmetics.

INDUSTRIAL APPLICABILITY

As described in detail above, the present invention can provide water-in-oil type emulsion cosmetics containing pigments. Such cosmetics are superior in makeup effects such as color development of cosmetics, covering power, and soft focus effect, have good moist feeling, and are superior in emulsion stability and pigment dispersibility.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A water-in-oil type emulsion cosmetic comprising:

(a) at least one polyaspartic acid or a salt thereof, (b) at least one spherical powder, (c) at least one oily component, (d) at least one lipophilic surfactant, (e) at least one pigment, and (f) water, wherein a content (Wa) of the (a) at least one polyaspartic acid or a salt thereof is 0.03 mass % to 0.9 mass % as a content of a free form thereof, based on the total mass of the cosmetic, the (b) at least one spherical powder is one or more members selected from the group consisting of spherical silicic anhydride, spherical silicone powder, spherical nylon powder, spherical cellulose powder, and spherical polyurethane powder, and has a volume-based average particle size of 0.5 μm to 20 μm, a content (Wb) of the (b) at least one spherical powder is 0.5 mass % to 3 mass %, based on the total mass of the cosmetic, and the (d) at least one lipophilic surfactant is one or more members selected from the group consisting of glycerol fatty acid ester, sorbitan fatty acid ester, and polyoxyethylene polyoxypropylene modified alkylmethylpolysiloxane dimethylpolysiloxane copolymer, each of which has a Hydrophilic-Lipophilic Balance (HLB) value of 3 to 6, and the emulsion cosmetic does not contain polyoxyethylene dipolyhydroxystrearate.

2. The emulsion cosmetic according to claim 1, wherein the (c) at least one oily component is one or more members selected from the group consisting of hydrocarbon, ester, and silicone oil.

3. The emulsion cosmetic according to claim 1, wherein a content ($W_c$) of the (c) at least one oily component is 5 mass % to 60 mass %, based on the total mass of the cosmetic.

4. The emulsion cosmetic according to claim 1, wherein a content ($W_d$) of the (d) at least one lipophilic surfactant is 0.1 mass % to 10 mass %, based on the total amount of the cosmetic.

5. The emulsion cosmetic according to claim 1, wherein the (e) at least one pigment is an inorganic pigment.

6. The emulsion cosmetic according to claim 1, further comprising (g) at least one hydrophilic or water-soluble additive for cosmetics.

7. The emulsion cosmetic according to claim 6, wherein the (g) at least one hydrophilic or water-soluble additive for cosmetics is one or more members selected from the group consisting of (g-1) at least one amino acid and a salt thereof, (g-2) at least one aliphatic hydroxycarboxylic acid having 1 to 10 carbon atoms and a salt thereof, (g-3) at least one polyhydric alcohol, and (g-4) at least one betaine.

8. The emulsion cosmetic according to claim 1, which has a viscosity of not less than 10 Pas at 25° C.

9. A method of making up skin, comprising applying a water-in-oil type emulsion cosmetic according to claim 1 to skin.

10. The method according to claim 9, wherein the (c) at least one oily component is one or more members selected from the group consisting of hydrocarbon, ester, and silicone oil.

11. The method according to claim 9, wherein a content ($W_c$) of the (c) at least one oily component in the cosmetic is 5 mass % to 60 mass %, based on the total mass of the cosmetic.

* * * * *